(12) United States Patent
Yamashita

(10) Patent No.: US 10,845,357 B2
(45) Date of Patent: Nov. 24, 2020

(54) OBSERVATION SYSTEM

(71) Applicant: OLYMPUS CORPORATION, Hachioji (JP)

(72) Inventor: Yusuke Yamashita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 178 days.

(21) Appl. No.: 16/150,753

(22) Filed: Oct. 3, 2018

(65) Prior Publication Data
US 2019/0107528 A1    Apr. 11, 2019

(30) Foreign Application Priority Data

Oct. 10, 2017   (JP) .................. 2017-196528

(51) Int. Cl.
| | |
|---|---|
| *G01N 33/483* | (2006.01) |
| *G06T 7/66* | (2017.01) |
| *G02B 21/36* | (2006.01) |
| *G06T 7/00* | (2017.01) |
| *G06T 7/70* | (2017.01) |
| *G01N 1/30* | (2006.01) |
| *G06K 9/52* | (2006.01) |
| *G06K 9/62* | (2006.01) |
| *G06K 9/00* | (2006.01) |

(52) U.S. Cl.
CPC ....... *G01N 33/4833* (2013.01); *G02B 21/365* (2013.01); *G06T 7/0012* (2013.01); *G06T 7/66* (2017.01); *G01N 1/30* (2013.01); *G06K 9/0014* (2013.01); *G06K 9/52* (2013.01); *G06K 9/6267* (2013.01); *G06T 7/70* (2017.01); *G06T 2200/04* (2013.01); *G06T 2207/30024* (2013.01)

(58) Field of Classification Search
CPC ........ G01N 33/4833; G01N 1/30; G06T 7/66; G06T 7/0012; G06T 7/70; G06T 2200/04; G06T 2207/30024; G06T 2207/10064; G06T 2207/10028; G06T 2207/10056; G02B 21/365; G06K 2209/05; G06K 9/52; G06K 9/6267; G06K 9/0014
USPC ........................................... 382/133
See application file for complete search history.

(56) References Cited

U.S. PATENT DOCUMENTS

| | | | | |
|---|---|---|---|---|
| 8,073,233 | B2 * | 12/2011 | Kanda .................. | G02B 21/365 382/133 |
| 2008/0279441 | A1 * | 11/2008 | Matsuo .............. | G01N 33/5008 382/133 |
| 2010/0083410 | A1 | 4/2010 | Hattori et al. | |

(Continued)

FOREIGN PATENT DOCUMENTS

| | | |
|---|---|---|
| JP | 2010085420 A | 4/2010 |
| JP | 2011179924 A | 9/2011 |
| JP | 2016223893 | 12/2016 |

*Primary Examiner* — Amandeep Saini
(74) *Attorney, Agent, or Firm* — Holtz, Holtz & Volek PC

(57) ABSTRACT

A fixed region at an outer periphery or an inner periphery of a sample that has a three-dimensional structure is selectively analyzed with accuracy. Provided is an observation system including a CPU that recognizes the 3D shape of an observation target, such as a spheroid, from a 3D image of cells, that sets a 3D mask of which the radial distance from a circumscribed surface of the recognized 3D shape is fixed over the entire region of the circumscribed surface and of which the shape is similar to the circumscribed surface, and that identifies a cell contained inside the set 3D mask.

8 Claims, 18 Drawing Sheets

(56) References Cited

U.S. PATENT DOCUMENTS

2011/0212486 A1    9/2011  Yamada et al.
2016/0350915 A1  12/2016  Takagi
2017/0278259 A1*  9/2017  Hattori ................. G02B 21/365

* cited by examiner

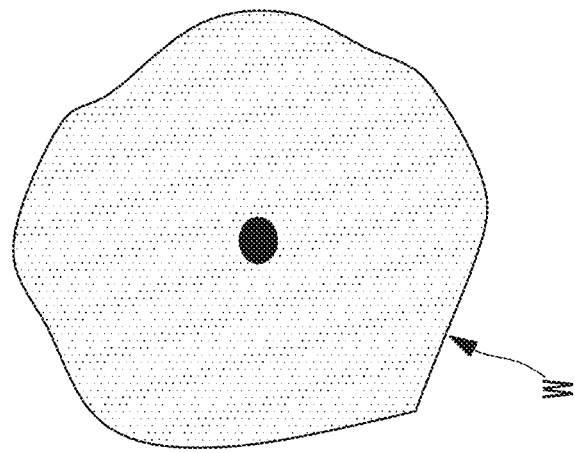
FIG. 4
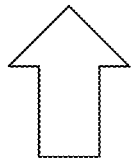
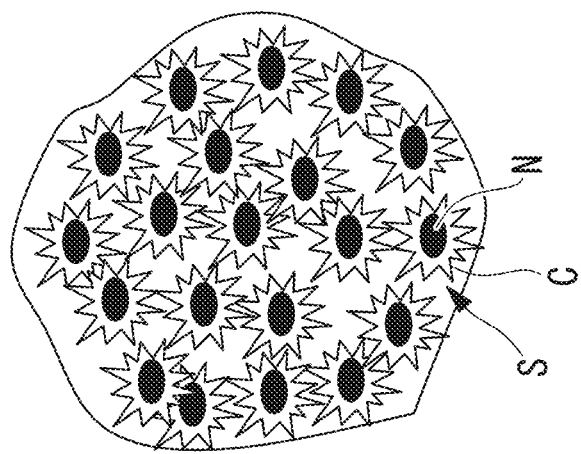

FIG. 6

RECOGNITION RESULTS – TABLE FOR CELL

| LABEL (OBJECT ID) | CENTER POSITION INFORMATION | CIRCUMSCRIBED RECTANGLE |
|---|---|---|
| 1 | $(X1, Y1, Z1)$ | $(X1\_d, Y1\_d, Z1\_d)$ |
| 2 | $(X2, Y2, Z2)$ | $(X2\_d, Y2\_d, Z2\_d)$ |
| 3 | $(X3, Y3, Z3)$ | $(X3\_d, Y3\_d, Z3\_d)$ |
| 4 | $(X4, Y4, Z4)$ | $(X4\_d, Y4\_d, Z4\_d)$ |
| ... | ... | ... |
| k | $(Xk, Yk, Zk)$ | $(Xk\_d, Yk\_d, Zk\_d)$ |
| ... | ... | ... |
| n | $(Xn, Yn, Zn)$ | $(Xn\_d, Yn\_d, Zn\_d)$ |

FIG. 7

RECOGNITION RESULTS – TABLE FOR SPHEROID

| LABEL (OBJECT ID) | CENTER-OF-GRAVITY POSITION INFORMATION | CIRCUMSCRIBED RECTANGLE |
|---|---|---|
| 1 | $(Xc, Yc, Zc)$ | $(X\_d, Y\_d, Z\_d)$ |

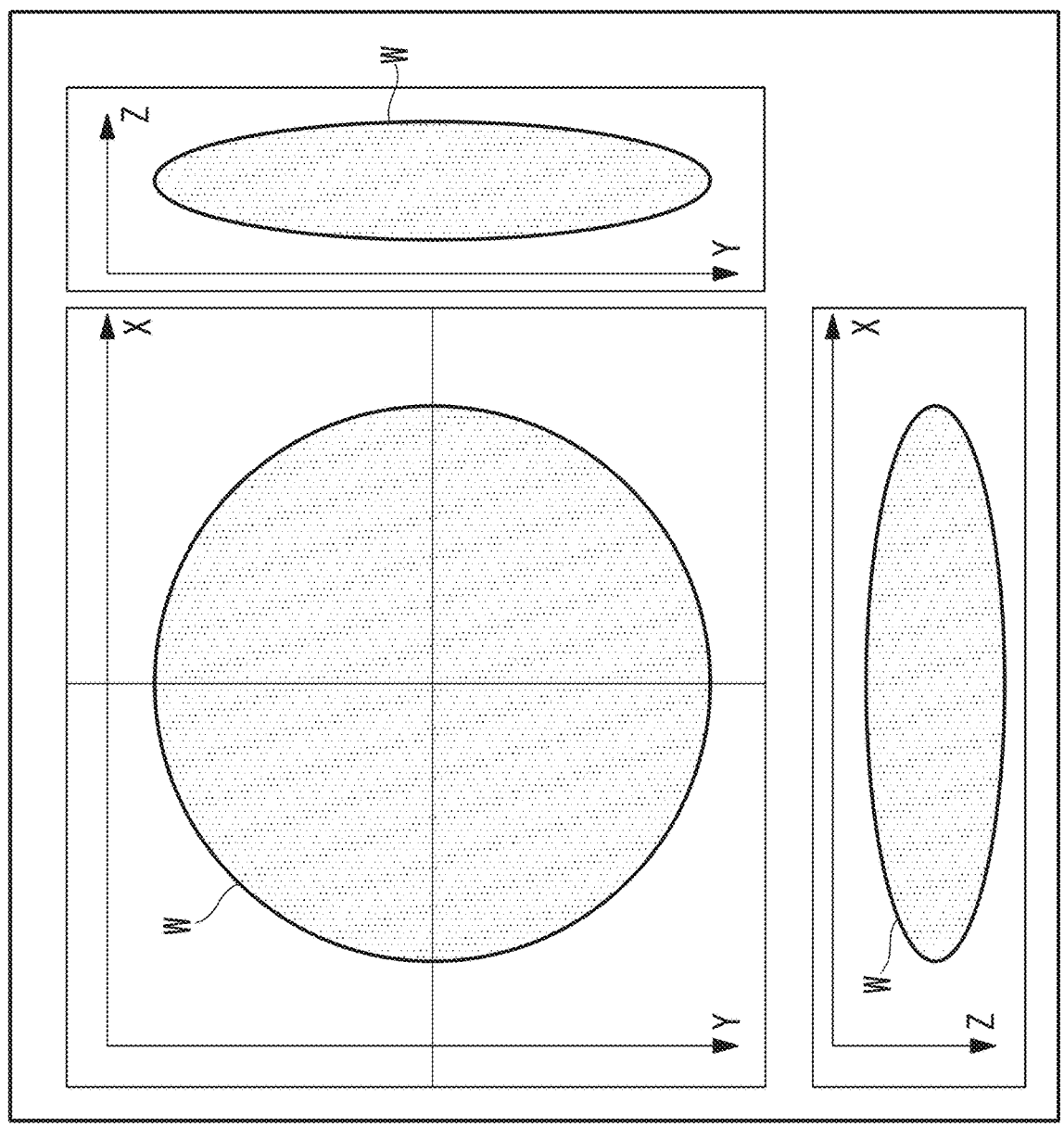
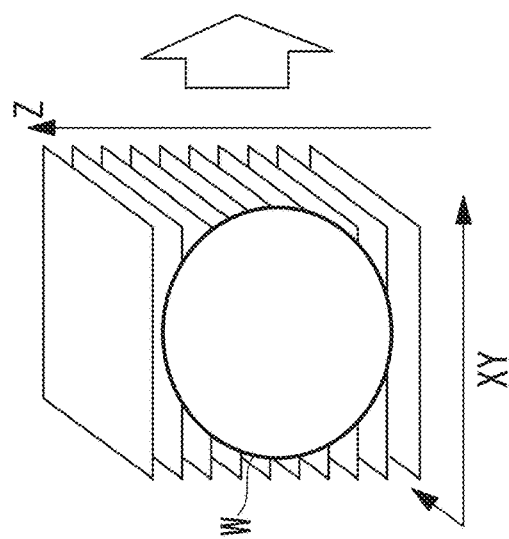
FIG. 10

OBSERVATION SYSTEM

CROSS-REFERENCE TO RELATED APPLICATIONS

This application is based on Japanese Patent Application No. 2017-196528, the contents of which are incorporated herein by reference.

TECHNICAL FIELD

The present invention relates to an observation system.

BACKGROUND ART

In the related art, in three-dimensional culturing in which cells are three-dimensionally cultured, there is a known observation system for observing the culture state of a cell cluster etc. that is formed by a plurality of cells cluster are aggregated three-dimensionally and that has a three-dimensional structure (for example, Japanese Unexamined Patent Application, Publication No. 2011-179924).

In the observation system described in Japanese Unexamined Patent Application, Publication No. 2011-179924, regions of cell components, such as a cell cluster, a nucleus, a cell membrane, and a cell cytoplasm, are recognized in a 2D fluorescence observation image on the basis of a pigment, each target site is recognized and extracted from the 2D fluorescence observation image on the basis of the amount of pigment, and the measurement value, e.g., the area, of the target site is output. Furthermore, in the observation system described in Japanese Unexamined Patent Application, Publication No. 2011-179924, in order to determine the appropriateness of recognition processing of a target site, the shape of the target site recognized on the 2D fluorescence observation image and the distribution on a histogram obtained from analysis results of the target site are both checked.

SUMMARY OF INVENTION

An object of the present invention is to provide an observation system capable of selectively analyzing, with accuracy, a fixed region at an outer periphery or an inner periphery of a sample that has a three-dimensional structure.

According to one aspect, the present invention provides an observation system including at least one processor that is provided with hardware, wherein the at least one processor performs control so as to: recognize the 3D shape of an observation target from a 3D image of a fluorescent specimen; set a similar region of which the distance in a radial direction from a circumscribed surface of the recognized 3D shape is fixed over the entire region of the circumscribed surface and of which the shape is similar to the circumscribed surface; and identify a cell that is contained inside the set similar region or a cell component that constitutes the cell.

The above-described aspect may further include a storage unit that stores at least one computer program to be executed by the at least one processor.

The above-described aspect may further include a thickness specifying unit that is configured to allow a user to specify a thickness in the radial direction of the similar region to be set, wherein the at least one processor may perform control so as to set the similar region according to the thickness specified by the user by means of the thickness specifying unit.

The above-described aspect may further include a distance specifying unit that is configured to allow a user to specify a distance in the radial direction from the circumscribed surface, which forms the similar region to be set, wherein the at least one processor may perform control so as to set the similar region according to the distance specified by the user by means of the distance specifying unit.

The above-described aspect may further include a display unit that simultaneously displays three cross-sectional images that constitute the 3D image and that are perpendicular to one another, in association with one another, wherein the at least one processor may further perform control so as to display the similar region and the cell that is contained inside the similar region or the cell component, in an overlapping manner on the respective cross-sectional images displayed by the display unit and so as to display the cell that is contained inside the similar region or the cell component and the cell that is contained outside the similar region or the cell component, in a distinguishable manner.

In the above-described aspect, the at least one processor may further perform control so as to extract the cell that is contained inside the similar region or the cell component and to output information about the extracted cell or cell component.

In the above-described aspect, the at least one processor may perform control so as to: recognize the 3D shape of a cell cluster formed by a plurality of cells cluster serving as the observation target; set the similar region inside the circumscribed surface of the cell cluster; and identify the cell that is contained inside the similar region.

In the above-described aspect, the at least one processor may perform control so as to: recognize the 3D shape of a nucleus of the cell that serving as the observation target; set the similar region outside the circumscribed surface of the nucleus of the cell; and identify the cell component that is contained inside the similar region.

According to another aspect, the present invention provides a non-transitory computer-readable medium that stores a computer-readable program for implementing a control method for controlling an observation system, the method including: a step of recognizing the 3D shape of an observation target from a 3D image of a fluorescent specimen; a step of setting a similar region of which the distance in a radial direction from a circumscribed surface of the recognized 3D shape is fixed over the entire region of the circumscribed surface and of which the shape is similar to the circumscribed surface; and a step of identifying a cell that is contained inside the set similar region or a cell component that constitutes the cell.

BRIEF DESCRIPTION OF DRAWINGS

FIG. 4 is a view for explaining how to recognize a spheroid from a cell cytoplasm.

FIG. 6 is a view showing an example table for cells.

FIG. 7 is a view showing an example table for a spheroid.

FIG. 10 is a view for explaining a state in which respective cross-sectional images of a 3D image of a spheroid are displayed in three planes.

DESCRIPTION OF EMBODIMENTS

First Embodiment

An observation system according to a first embodiment of the present invention will be described below with reference to the drawings.

Figure 1:
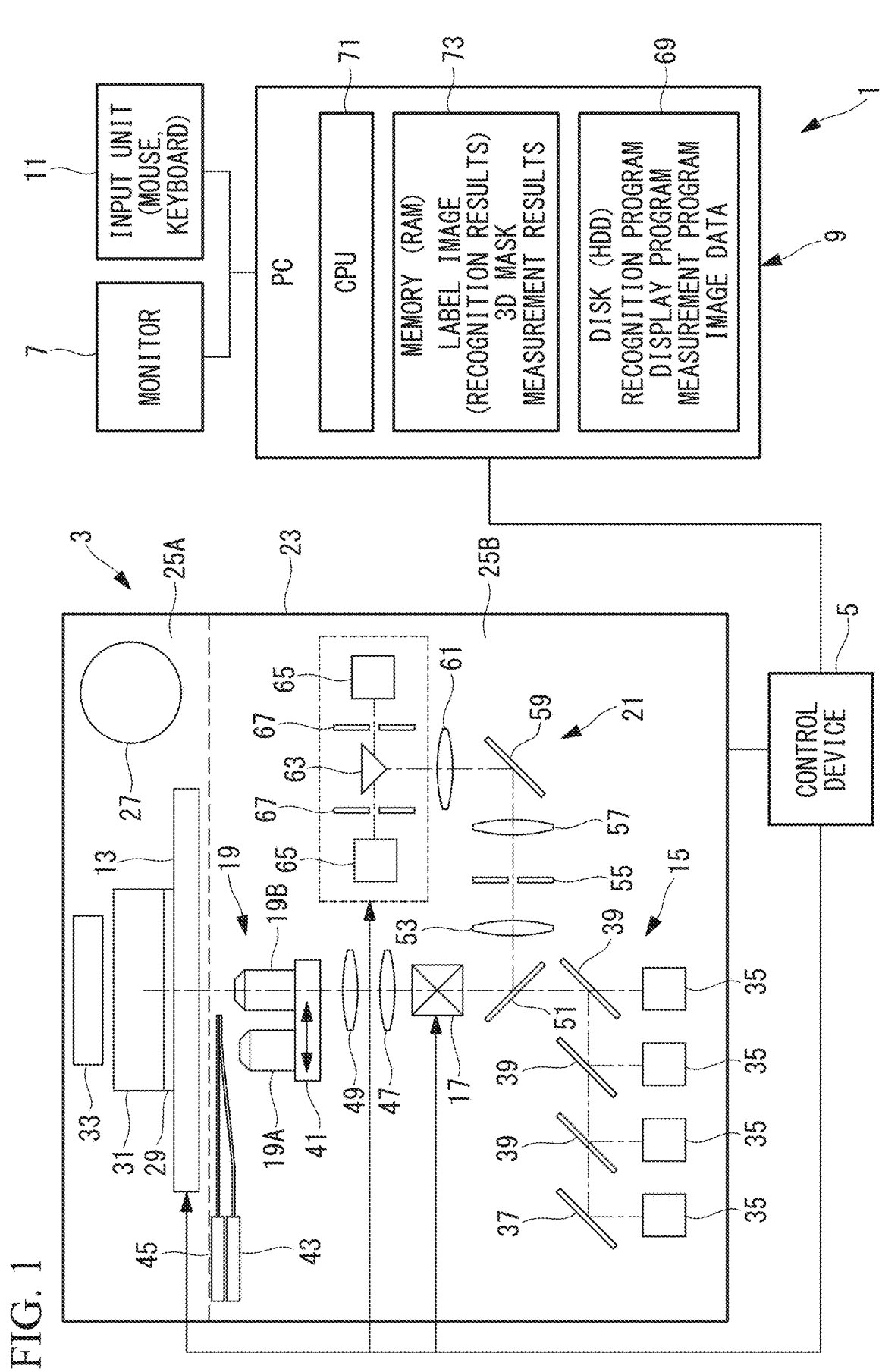
FIG. 1 is a view showing, in outline, the configuration of an observation system according to a first embodiment of the present invention.

As shown in FIG. 1, an observation system 1 of this embodiment is provided with: a laser scanning microscope 3; a control device 5 that controls the laser scanning microscope 3 and that constructs an image; a monitor (display unit) 7 that displays the image constructed by the control device 5; a PC (Personal Computer) 9; and an input unit (thickness specifying unit) 11, such as a mouse or a keyboard, through which a user performs various inputs.

Figure 2:
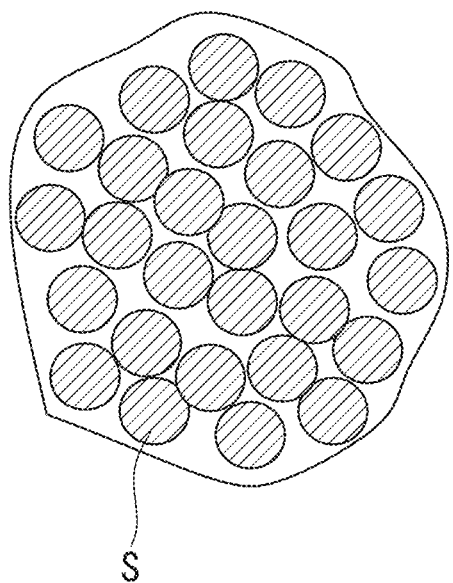
FIG. 2 is a view for explaining recognition of cells.
Figure 3:
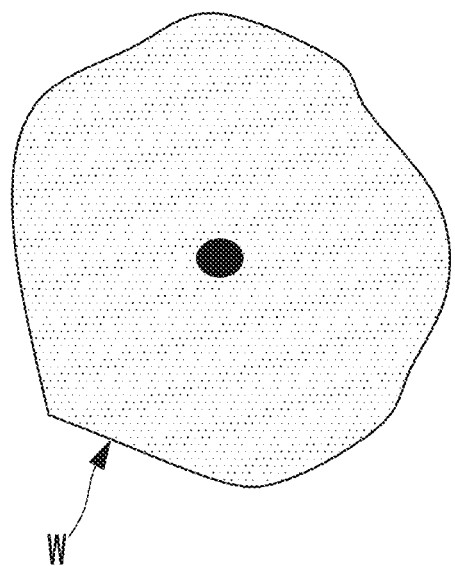
FIG. 3 is a view for explaining recognition of a spheroid.

The laser scanning microscope 3 is provided with: a motorized stage 13 on which is mounted a transparent container (not shown), such as a petri dish, for containing a spheroid (cell cluster) W composed of a plurality of cells (fluorescent specimens) S shown in FIGS. 2 and 3; a laser light source unit 15 that emits laser light; a scanner 17 that two-dimensionally scans the laser light emitted by the laser light source unit 15; an objective lens 19 that focuses the laser light scanned by the scanner 17 onto a cell S; an image acquisition unit 21 that detects fluorescence produced in the cell S when the cell S is irradiated with the laser light through the objective lens 19 and that acquires an image of the cell S; and a dark box 23 that accommodates the above components of the laser scanning microscope 3.

The motorized stage 13 is provided with three motors (not shown), so that the motorized stage 13 moves independently along motion axes in X, Y, and Z directions perpendicular to one another, thus making it possible to move the container mounted thereon in three-dimensional directions.

The interior of the dark box 23 is divided into an upper area 25A, which includes the motorized stage 13, and a lower area 25B, which is located lower than the upper area 25A. A heater 27 is disposed in the upper area 25A, so that the temperature in the upper area 25A is adjusted to predetermined culture conditions (for example, 27° C.±0.5° C.). A sample holder 29 that is mounted on the motorized stage 13 in a positioned state is disposed in the upper area 25A.

The sample holder 29 can hold, on the motorized stage 13, the container in a positioned state. The container held by the sample holder 29 is accommodated in a simple incubator 31, thus maintaining the culture conditions thereof (for example, humidity of 100% and $CO_2$ concentration of 0.5%). In the figure, reference sign 33 denotes a phase-difference capacitor for phase-difference observation.

The laser light source unit 15 is provided with: a plurality of laser diodes 35 that produce laser light at different wavelengths; and a mirror 37 and dichroic mirrors 39 that cause the laser light produced by the plurality of laser diodes 35 to merge into a single light path.

The scanner 17 is, for example, a so-called proximity galvanometer mirror that is formed by opposing two galvanometer mirrors that are made to swivel about axes perpendicular to each other.

The objective lens 19 is provided such that it is possible to switch between an objective lens 19A for dry observation and an objective lens 19B for oil-immersion or water-immersion observation by means of a revolver 41. The objective lens 19 has an auto-focus function and detects an in-focus position periodically or as needed. The objective lens 19 is moved in the direction along the optical axis, thereby making it possible to match the focus position of the objective lens 19 with the surface of the cell S.

In the figure, reference sign 43 denotes a pump for supplying immersion oil for oil immersion or water for water immersion to the space between the objective lens 19B and the bottom of the container, and reference sign 45 denotes an airbrush for removing the water or the immersion oil.

A pupil projection lens 47 and an imaging lens 49 that focus the laser light scanned by the scanner 17 are disposed between the scanner 17 and the objective lens 19.

The image acquisition unit 21 is provided with: a beam splitter 51 that is inserted between the laser light source unit 15 and the scanner 17 and that splits off, from the light path of the laser light, fluorescence that is produced by the cell S and that returns via the objective lens 19, the imaging lens 49, the pupil projection lens 47, and the scanner 17; a confocal lens 53 that focuses the fluorescence split off by the beam splitter 51; a variable pinhole 55; a collimating lens 57; a grating 59 that diffracts the fluorescence converted into approximately collimated light by the collimating lens 57, thus separating the fluorescence into wavelengths; a focusing lens 61 that focuses the fluorescence separated by the grating 59; a beam splitter 63 that splits the focused fluorescence into wavelengths; and light detectors 65 that respectively detect the fluorescence split by the beam splitter 63. The variable pinhole 55 is disposed in an optically conjugate positional relationship with the focus position of the objective lens 19. Reference sign 67 denotes pinholes.

The control device 5 controls driving of the motorized stage 13 and the scanner 17 and constructs an image on the basis of luminance information output from the light detectors 65. For example, the control device 5 moves the stage 8 three-dimensionally with respect to the objective lens 19, thereby moving a spheroid W three-dimensionally with respect to the focus position of the objective lens 19, and, at the same time, the control device 5 causes the scanner 17 to two-dimensionally scan the laser light at each focus position. Then, a slice image (acquired image) of a cell S that is disposed at the focus position of the objective lens 19 is constructed on the basis of a luminance signal output from the light detector 65 that has detected the fluorescence produced by the cell S. In this way, a plurality of slice images of each cell S are acquired.

Then, the control device 5 subjects the plurality of slice images of each cell S to image processing, thereby constructing a 3D image of the entire spheroid W. Data for the plurality of slice images and the 3D image obtained by the control device 5 is sent to the PC 9.

The control device 5 is constituted of: a first communication I/F circuit (not shown) for performing data communication with the PC 9; a second communication I/F circuit (not shown) for performing data communication with the laser scanning microscope 3 in order to control the motorized stage 13, the scanner 17, the light detectors 65, etc.; a CPU (Central Processing Unit, not shown); a memory (not shown); and so on. Note that, in order to efficiently generate a 3D image, a GPU (Graphics Processing Unit, not shown) may be provided separately from the CPU.

The PC 9 is provided with: a disk (HDD (Hard Disk Drive), storage unit) 69 that stores various programs, image data, graph data, etc.; a CPU (Central Processing Unit, shape recognition unit, similar-region setting unit, identifying unit, display control unit, extraction unit) 71 that executes the programs stored in the disk 69; and a memory 73, such as a RAM (Random Access Memory), that stores recognition results and analysis results of the cells S obtained through the execution of the programs in the CPU 71.

The disk 69 stores, as the programs to be executed by the CPU 71, a recognition program, a display program, a 3D-mask generation program (not shown), and a measurement program, for example. The disk 69 stores image data, such as a plurality of slice images of each cell S and a 3D image of the entire spheroid W, acquired by the control device 5.

Through the execution of the recognition program, the CPU 71 performs recognition processing with respect to individual cells S and a spheroid W on a 3D image. In the recognition processing, for example, a plurality of LoG (Laplacian Of Gaussian) filters having different sizes are adopted, a local peak position and the size thereof are detected from output values of the LoG filters, and this peak position is set as a seed (the center position of the cell S). Then, the LoG filters are applied two-dimensionally and three-dimensionally, and the results are combined. Next, trimming and, adaptively, binarization processing are applied to a neighborhood region around the seed on the basis of the size thereof, thus forming a region of the recognized cell S, as shown in FIG. 2. A cluster of a plurality of recognized cells S is recognized as a single aggregation (spheroid W), and, as shown in FIG. 3, a region that circumscribes the plurality of cells S, i.e., a region of the recognized spheroid W, is formed. As shown in FIG. 4, it is also possible to recognize a cell cytoplasm C and to recognize a cluster of recognized cell cytoplasms C as a single spheroid W.

Figure 5:
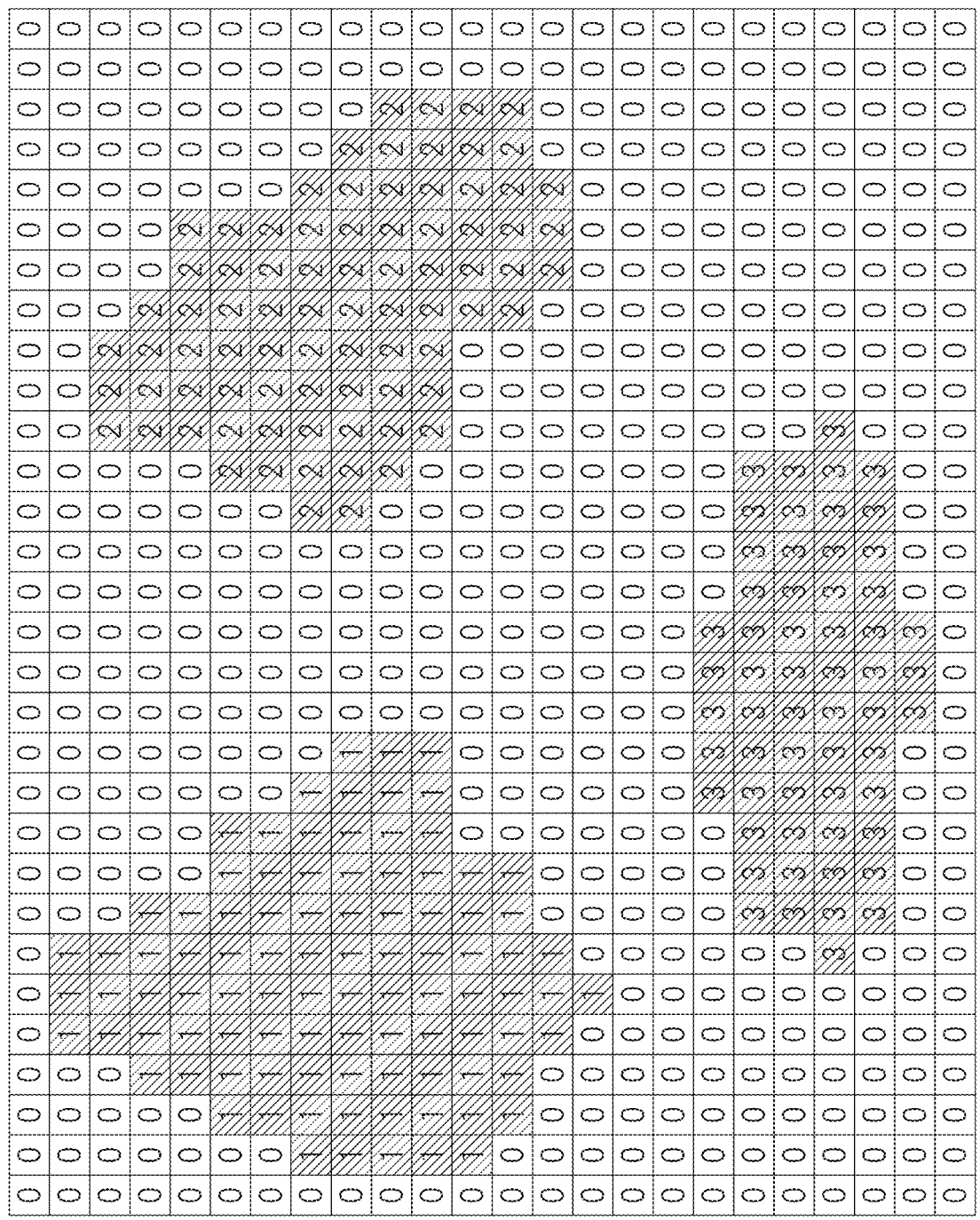
FIG. 5 is a view showing an example label image.

The CPU 71 identifies the recognized individual cells S and spheroid W by assigning, thereto, labels different from one another, thus generating, for example, a label image, such as that shown in FIG. 5, a table for the individual cells S, such as that shown in FIG. 6, and a table for the spheroid W, such as that shown in FIG. 7.

As shown in FIG. 5, the label image is a 2D image that expresses recognized cells S respectively assigned, as the labels, object IDs (for example, 1, 2, 3, 4, . . . , k, . . . , n) and an unrecognized background assigned 0. The table for the cells S is information in which the labels (object IDs), which are assigned to the individual cells S, the center position information thereof, and the circumscribed rectangles thereof are associated, as shown in FIG. 6. The table for the spheroid W is information in which the label (object ID), which is assigned to the spheroid W, the center-of-gravity position information thereof, and the circumscribed rectangle thereof are associated, as shown in FIG. 7. The label image and the tables generated by the CPU 71 are stored in the memory 73.

Figure 8:
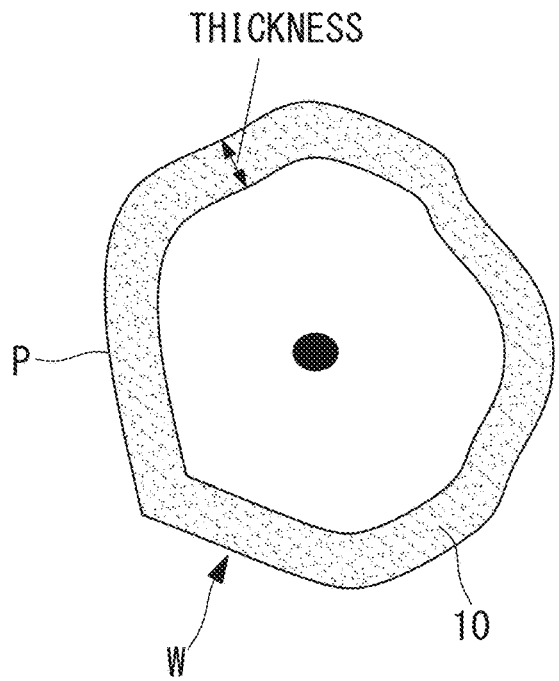
FIG. 8 is a view showing an example 3D mask that is set inside a spheroid.

Through the execution of the 3D-mask generation program, as shown in FIG. 8, the CPU 71 sets a 3D mask (similar region) 10 of which the radial distance from a circumscribed surface P of a 3D shape of the recognized spheroid W is fixed over the entire region of the circumscribed surface P and of which the shape is similar to the circumscribed surface P. Specifically, according to the radial thickness of the 3D mask 10 specified by the user by means of the input unit 11, the CPU 71 sets, inside the spheroid W, a 3D mask 10 that extends inward from the circumscribed surface P by the corresponding thickness over the entire region of the circumscribed surface P.

Figure 9:
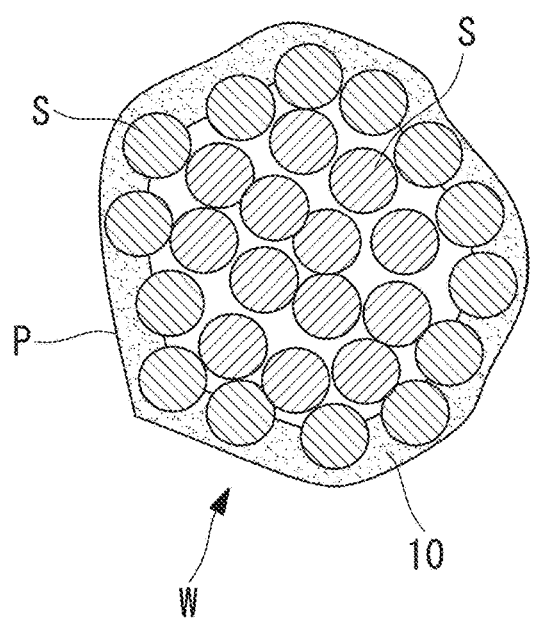
FIG. 9 is a view for explaining a state in which cells that overlap with the 3D mask shown in FIG. 8 are identified and extracted.

Through the execution of the measurement program, the CPU 71 identifies cells S that are contained inside the set 3D mask 10, i.e., cells S that overlap with the 3D mask 10, and extracts the corresponding cells S, as shown in FIG. 9. For example, the CPU 71 may extract cells S of which the centers of gravity of the nuclei are contained inside the 3D mask 10. The CPU 71 creates data (information) about the extracted cells S. The data about the cells S includes the number of cells, the brightness value, and the length of a long axis, for example. Then, the CPU 71 creates graphs showing the created data and displays the graphs on the monitor 7. The graphs include a histogram, a scattergram, and a line graph, for example. The graphs created by the CPU 71 are stored in the disk 69.

Through the execution of the display program, the CPU 71 simultaneously displays three cross-sectional images, i.e., an XY cross-sectional image, an XZ cross-sectional image, and a YZ cross-sectional image, that constitute a 3D image and that are perpendicular to one another, on the monitor 7 in an associated manner, for example, as shown in FIG. 10 (three-plane display). The respective cross-sectional images correspond to an acquired image in the XY direction and 2D images formed of cross sections obtained by cutting a 3D image in the XZ direction and the YZ direction.

Figure 11:
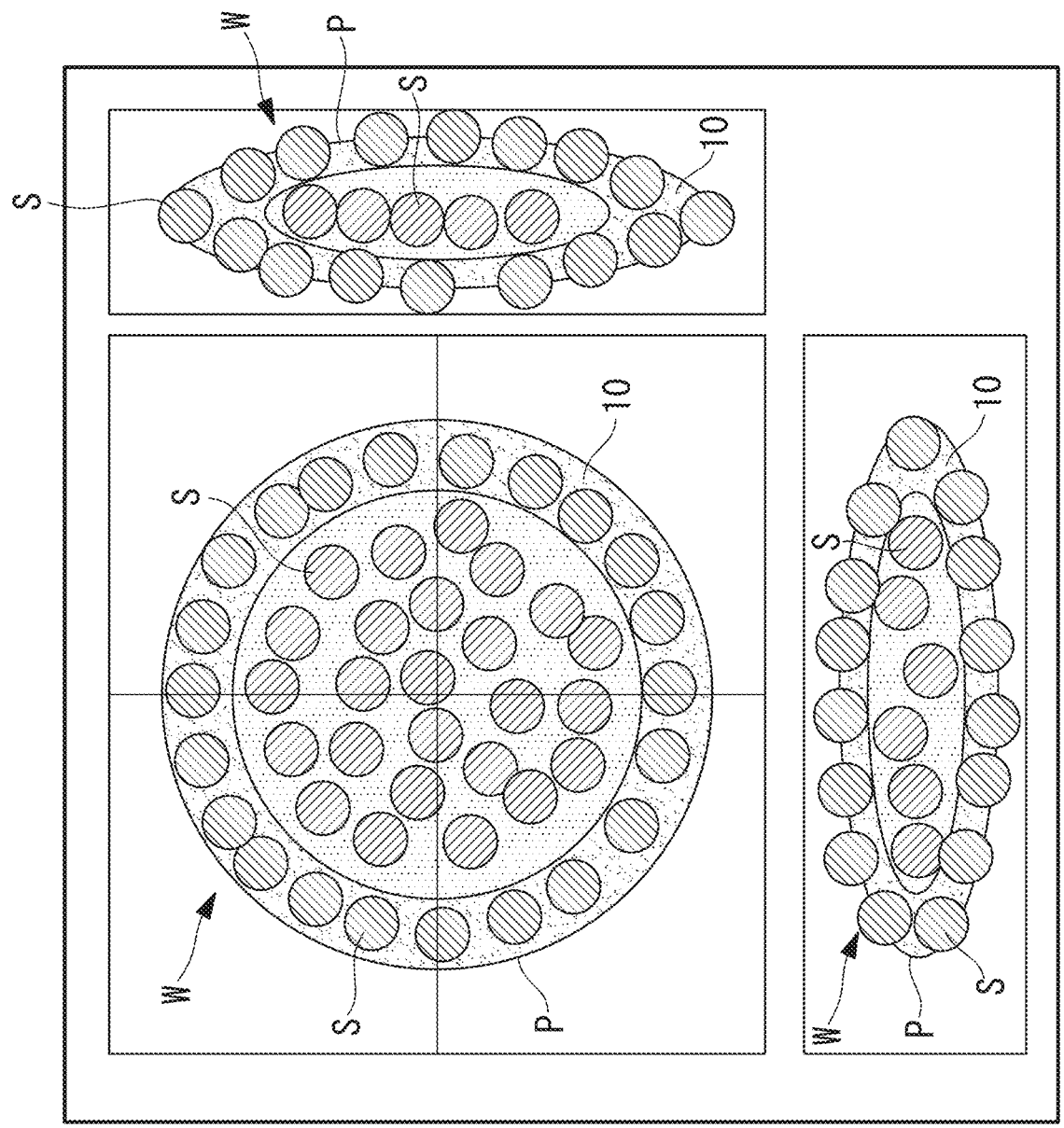
FIG. 11 is a view for explaining a state in which a 3D mask and cells are displayed on the respective cross-sectional images shown in FIG. 10, in a distinguishable manner.

As shown in FIG. 11, the CPU 71 displays the 3D mask 10 and the cells S that are contained inside the 3D mask 10 in an overlapping manner on the respective cross-sectional images displayed on the monitor 7 and also displays the cells S that are contained inside the 3D mask 10 and the cells S that are contained outside the 3D mask 10 in a distinguishable manner. For example, the CPU 71 displays the region of the spheroid W where the 3D mask 10 is set, the region of the spheroid W where the 3D mask 10 is not set, the cells S that are contained inside the 3D mask 10, and the cells S that are contained outside the 3D mask 10, in different colors, respectively.

Figure 12:
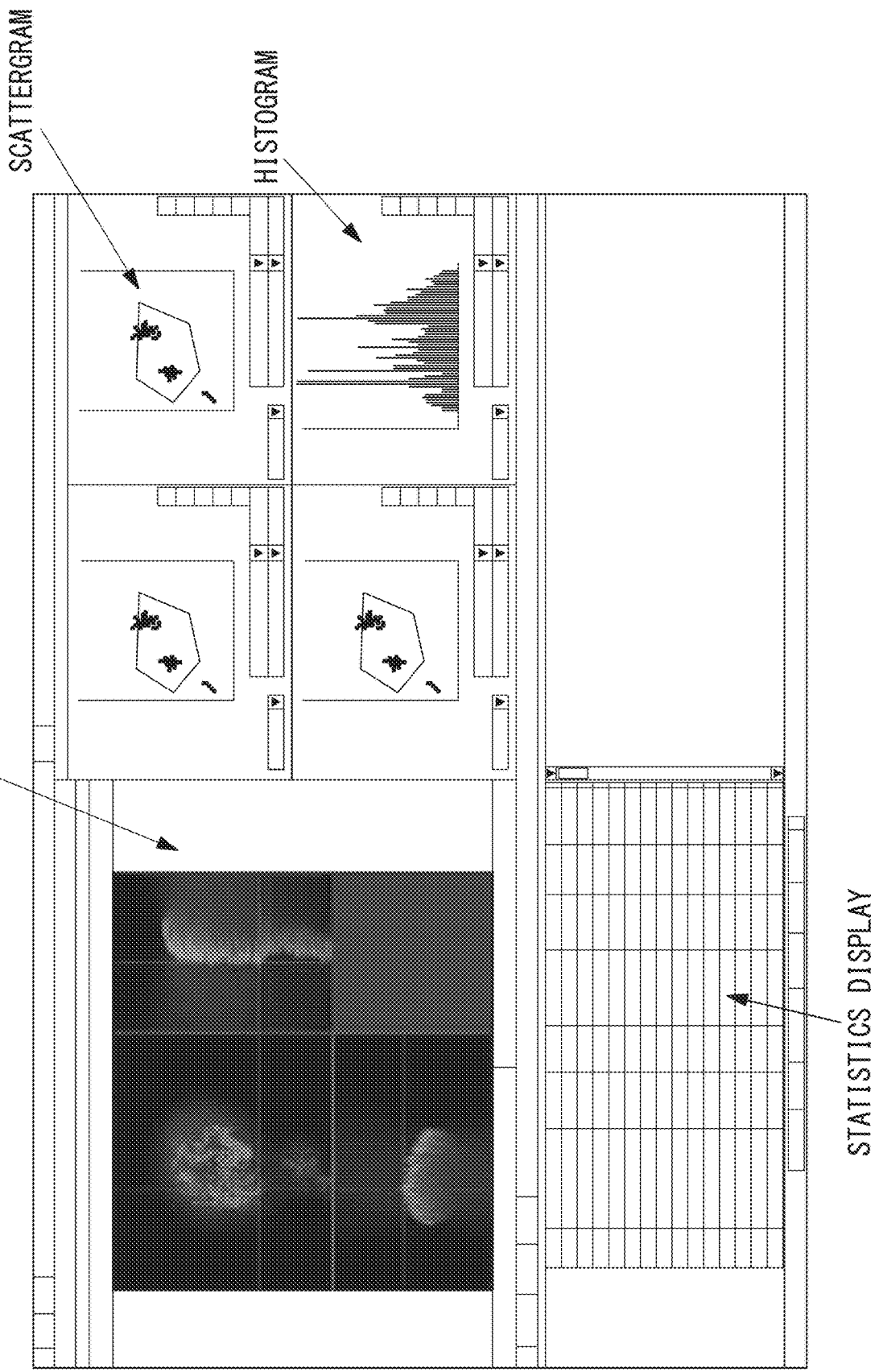
FIG. 12 is a view showing a state in which the respective cross-sectional images and graphs are displayed side by side on a monitor.

As shown in FIG. 12, the monitor 7 can display, side by side, the three cross-sectional images, which constitute a 3D image and which are perpendicular to one another, and the graphs, such as a histogram and a scattergram.

Figure 13:
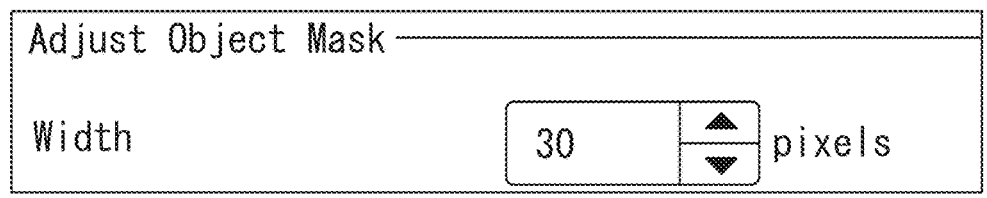
FIG. 13 is a view for explaining a state in which the thickness of a 3D mask is specified by means of an input unit.

As shown in FIG. 13, with the input unit 11, the user can specify the thickness of a 3D mask 10, in the direction along the radial direction of the spheroid W, that is to be set by the CPU 71 (width; hereinafter, referred to as the thickness of the 3D mask 10 in this embodiment). The thickness of the 3D mask 10 may be indicated in terms of the number of pixels or the distance, for example. FIG. 13 shows an example case in which the thickness of the 3D mask 10 is indicated in terms of the number of pixels.

The operation of the thus-configured observation system 1 will now be described.

First, a description will be given of a case in which a 3D image of cells S is acquired by using the observation system 1 of this embodiment.

First, the container is held by the sample holder 29, the container is mounted on the motorized stage 13, and the laser light source unit 15 is made to produce laser light.

The laser light produced by the laser light source unit 15 is two-dimensionally scanned by the scanner 17 and is focused on a cell S in the container via the pupil projection lens 47, the imaging lens 49, and the objective lens 19. At the position irradiated with the laser light, a fluorescent substance existing in the cell S is excited to produce fluorescence. The produced fluorescence returns along the light path of the laser light via the objective lens 19, the imaging lens 49, the pupil projection lens 47, and the scanner 17 and is split off therefrom by the beam splitter 51, thus entering the image acquisition unit 21.

The fluorescence entering the image acquisition unit 21 is focused by the confocal lens 53, and only fluorescence that has passed through the variable pinhole 55 is converted into substantially collimated light by the collimating lens 57. Then, the fluorescence is diffracted by the grating 59, travels via the focusing lens 61 and the beam splitter 63, and is detected by the different light detectors 65 for respective wavelengths. Then, in the control device 5, slice images of the cell S are constructed on the basis of luminance signals output from the light detectors 65, and the plurality of constructed slice images are subjected to image processing, thus constructing a 3D image.

In this case, the variable pinhole 55 is sufficiently narrowed down, thereby making it possible to allow only fluorescence that is produced at the focus position of the objective lens 19 to pass therethrough and to be detected by the light detectors 65, and to acquire a clear confocal fluorescence image.

Next, a description will be given of a case in which a desired spheroid W is observed by using the observation system 1 of this embodiment.

First, the CPU 71 executes the display program and displays the XY cross-sectional image, the XZ cross-sectional image, and the YZ cross-sectional image, which constitute a 3D image of the spheroid W, and the graphs, on the monitor 7 side by side in association with one another.

Figure 14:
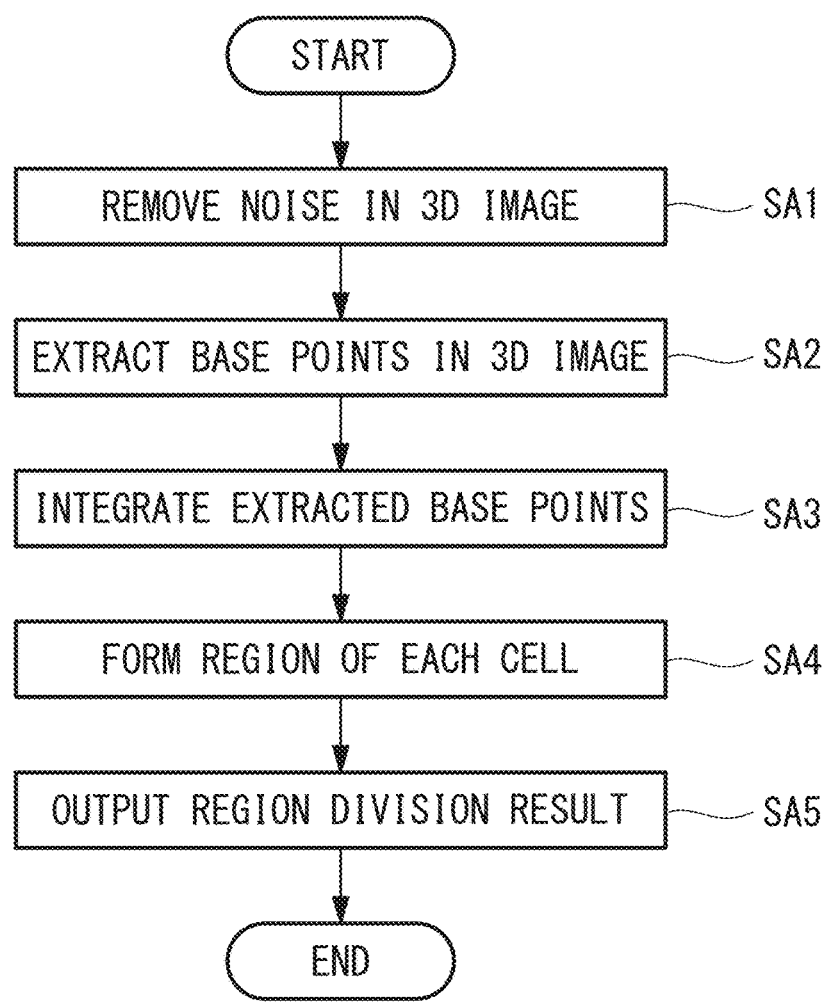
FIG. 14 is a flowchart for explaining cell recognition processing.

As shown in the flowchart of FIG. 14, the CPU 71 executes the recognition program. Specifically, noise in the 3D image of the spheroid W, which is stored in the disk 69, is removed (Step SA1), and base points based on binarization are extracted from the 3D image (Step SA2). Then, the extracted base points are integrated (Step SA3), a region of each cell S is formed (Step SA4), and the formed region of the cell S is divided, and the division result is output (Step SA5).

Then, the CPU 71 recognizes the individual cells S on the 3D image, identifies the cells S by assigning, thereto, labels different from one another, and generates a label image, such as that shown in FIG. 5, and a table for the cells S, such as that shown in FIG. 6. The CPU 71 recognizes a cluster of a plurality of cells S as a single spheroid W, assigns a label thereto, and generates a table for the spheroid W, such as that shown in FIG. 7.

Figure 15:
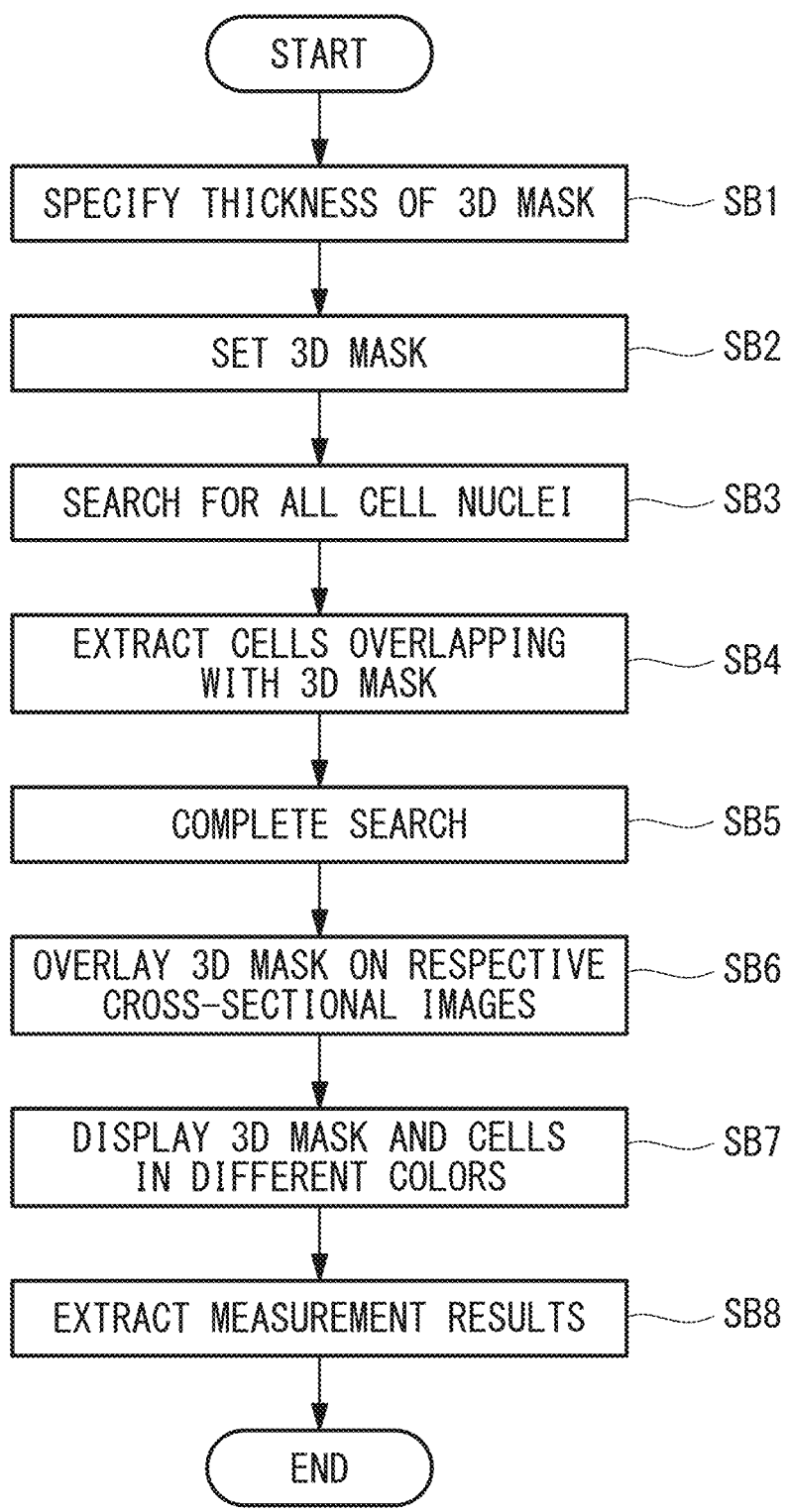
FIG. 15 is a flowchart for explaining 3D-mask generating processing.

Then, as shown in the flowchart of FIG. 15, the CPU 71 executes the 3D-mask generation program. Specifically, first, when the user specifies the thickness of the 3D mask 10 by means of the input unit 11 (Step SB1), the CPU 71 sets a 3D mask 10 that extends inward from the circumscribed surface P by the corresponding thickness over the entire region of the circumscribed surface P of the spheroid W, according to the thickness specified by the user, as shown in FIG. 8 (Step SB2).

Then, the CPU 71 executes the measurement program, thus starting to search for the nuclei of all labelled cells S, in the label image and the tables for the cells S and the spheroid W, which are stored in the disk 69 (Step SB3). Then, as shown in FIG. 9, cells S that overlap with the set 3D mask 10, i.e., cells S of which the centers of gravity of the nuclei are contained inside the 3D mask 10, are extracted (Step SB4). When all cells S that overlap with the 3D mask 10 are extracted, the searching ends (Step SB5).

Then, the CPU 71 executes the display program, and the 3D mask 10 is overlaid on the XY cross-sectional image, the XZ cross-sectional image, and the YZ cross-sectional image, which are displayed on the monitor 7 (Step SB6). Then, as shown in FIG. 11, the CPU 71 displays, in the respective cross-sectional images, a region where the 3D mask 10 is set, a region where the 3D mask 10 is not set, cells S that overlap with the 3D mask 10, cells S that do not overlap with the 3D mask 10, in different colors in a distinguishable manner (Step SB7).

Figure 16:
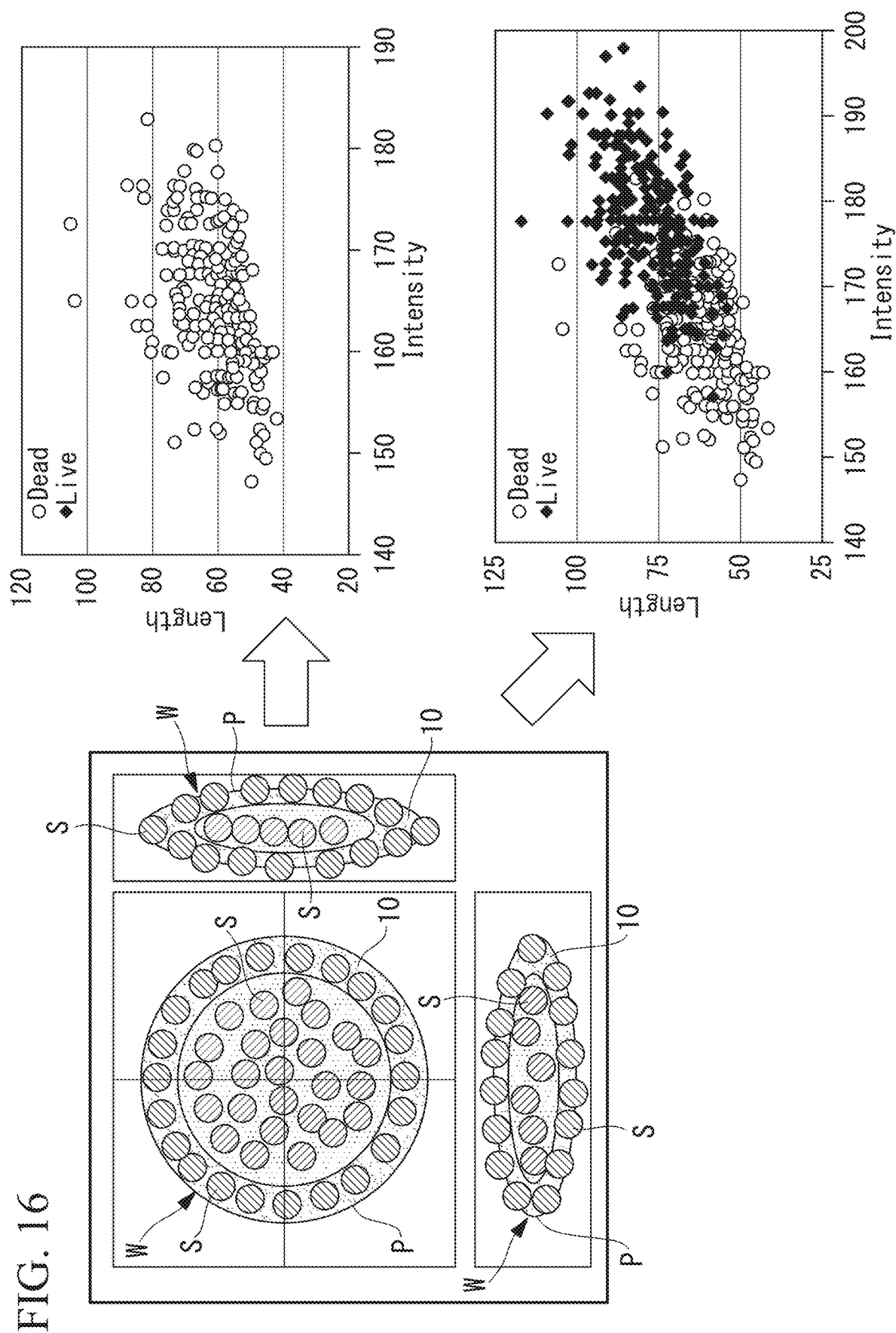
FIG. 16 is a view showing: an example graph indicating the relationship between the brightness value and the size, for only cells that overlap with the 3D mask; and an example graph indicating the relationship between the brightness value and the size, for both cells that overlap with the 3D mask and cells that do not overlap therewith.

The CPU 71 executes the measurement program, and, as a result of measurement of the cells S that overlap with the 3D mask 10, for example, the number of the corresponding cells is measured and displayed on the monitor 7 (Step SB8). As shown in FIG. 16, only the nuclei of the cells S that overlap with the 3D mask 10 (the nuclei of the dead cells S) may be displayed in a graph, or the nuclei of the cells S that overlap with the 3D mask 10 (the nuclei of the dead cells S) and the nuclei of the cells S that do not overlap therewith (the nuclei of the live cells S) may be displayed in a graph in different colors in a distinguishable manner. In FIG. 16, the vertical axis indicates the size of the nucleus of a cell S (the length of a long axis, Length), and the horizontal axis indicates the brightness value (Intensity) of the nucleus of a cell S. In FIG. 16, a graph in the upper right in the figure displays only the nuclei of the cells S that overlap with the 3D mask 10 (the nuclei of the dead cells S), and a graph in the lower right displays the nuclei of the cells S that overlap with the 3D mask 10 (the nuclei of the dead cells S) and the nuclei of the cells S that do not overlap therewith (the nuclei of the live cells S) in different colors.

Here, because the shape of a spheroid W is not always spherical, if the interior of a fixed region from the center of gravity of a spheroid W in the radial direction over the entire region in the circumferential direction is set, as a 3D mask, with reference to the center of gravity of the spheroid W, for example, the distance from the circumscribed surface P of the spheroid W varies for the individual cells S that overlap with the 3D mask.

In contrast to this, according to the observation system 1 of this embodiment, with reference to the circumscribed surface P of the 3D shape of the spheroid W, a 3D mask 10 that has a fixed radial distance from the circumscribed surface P toward the inner side over the entire region of the circumscribed surface P is set, and cells S that overlap with the 3D mask 10 are identified, thereby making it possible to distinguish cells S that exist within the fixed distance from the circumscribed surface P, from cells S that exist in the other locations. Therefore, cells S that exist in the fixed region inside the spheroid W, which has a three-dimensional structure, can be analyzed with accuracy.

Accordingly, for example, when a drug is administered to an outer section of the spheroid W, the drug infiltrates toward the inside of the spheroid W, so that the effect of the drug with respect to the cells S that exist within the fixed distance from the circumscribed surface P of the spheroid W can be correctly evaluated, separately from the effect of the drug with respect to the cells S that exist in the other locations.

Figure 17:
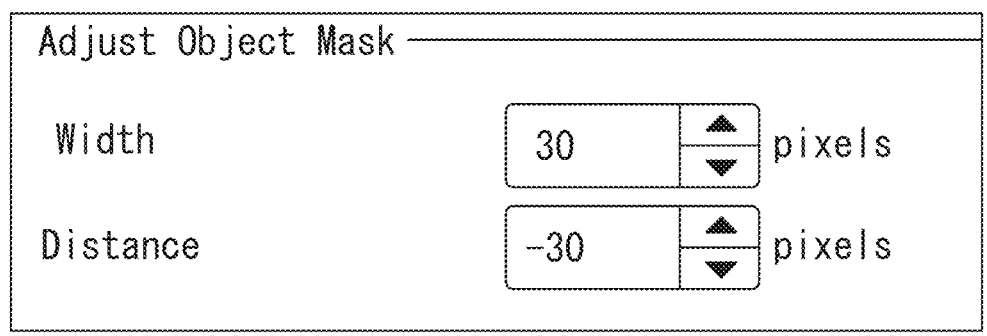
FIG. 17 is a view for explaining a state in which the thickness and the distance of a 3D mask are specified by means of the input unit.

In this embodiment, although a description has been given of an example case in which the user specifies only the thickness of the 3D mask 10, and the CPU 71 sets a 3D mask 10 that extends inward from the circumscribed surface P of the spheroid W by the thickness specified by the user, instead of this, it is also possible for the user to specify, in addition to the thickness of the 3D mask 10, the radial distance from the circumscribed surface P of the spheroid W at which the 3D mask 10 is to be set (Distance; hereinafter, referred to as the distance of the 3D mask 10, in this modification), as shown in FIG. 17, and for the CPU 71 to set a 3D mask 10 according to the thickness and the distance specified by the user.

Figure 18:
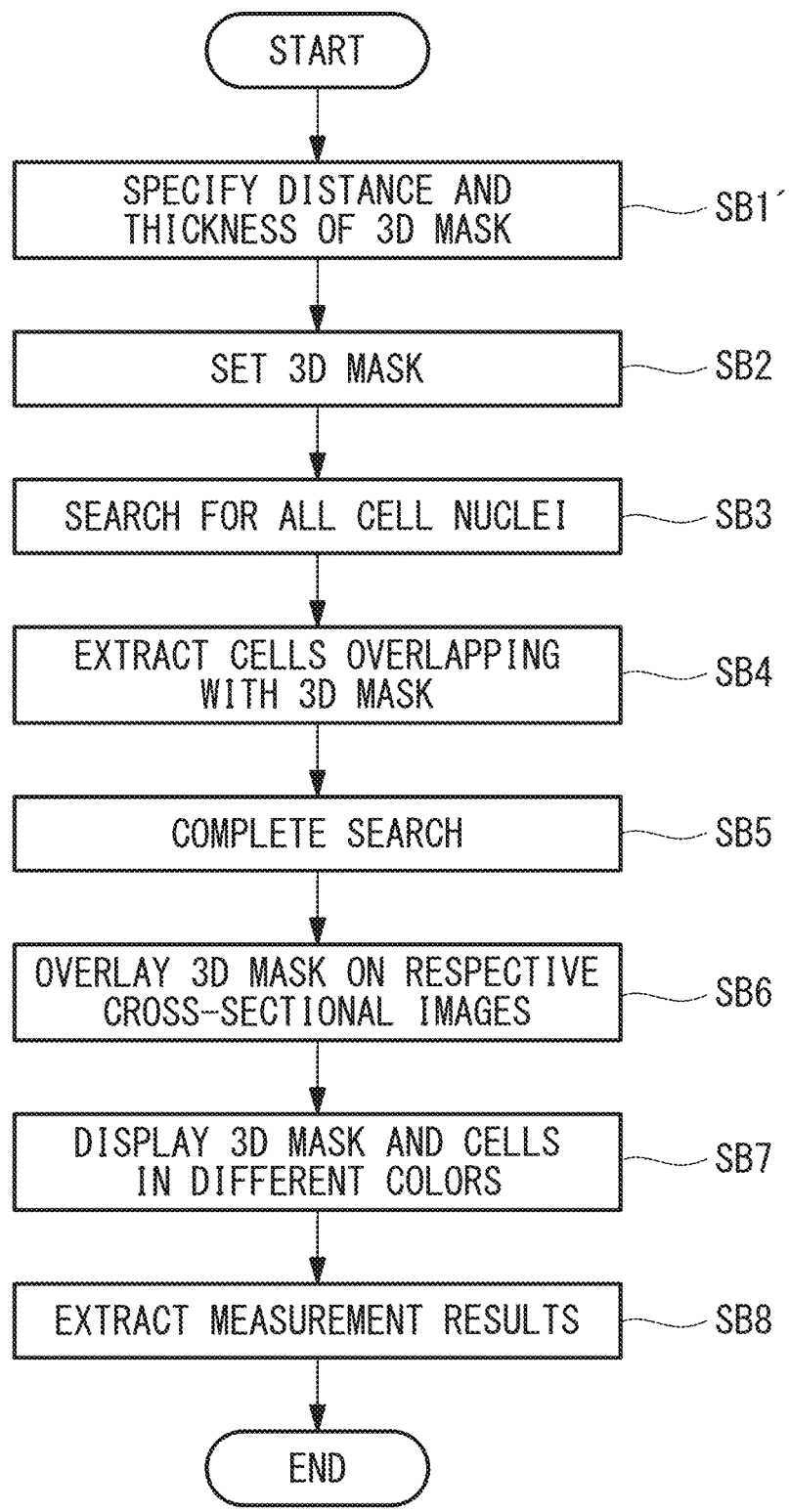
FIG. 18 is a flowchart for explaining 3D-mask generating processing performed by an observation system according to a modification of the first embodiment of the present invention.
Figure 19:
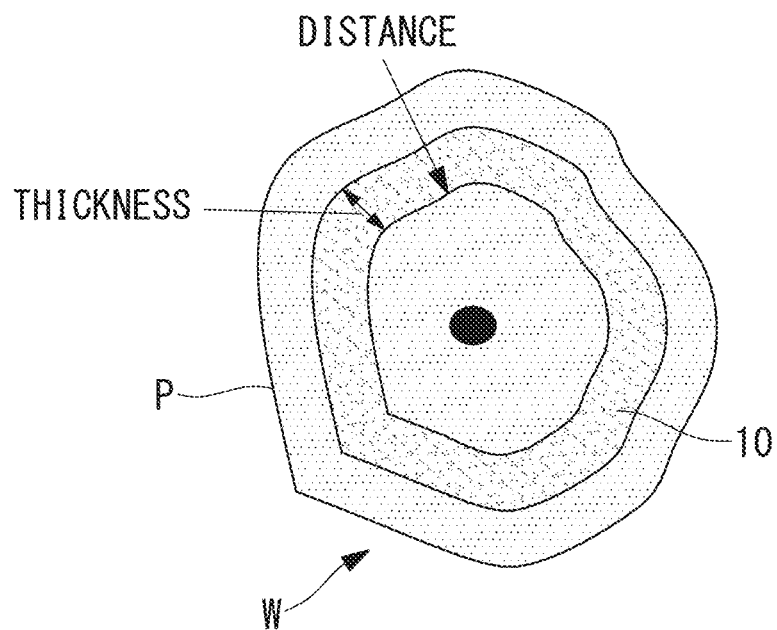
FIG. 19 is a view showing an example 3D mask that is set, inside a spheroid, by specifying the radial distance and the thickness.

In this case, the input unit 11 functions as the thickness specifying unit and a distance specifying unit. Then, as shown in the flowchart of FIG. 18, when the user specifies the distance and the thickness by means of the input unit 11 (Step SB1'), the CPU 71 sets a 3D mask 10 that extends inward by the corresponding thickness at the position shifted from the circumscribed surface P by the corresponding distance over the entire region of the circumscribed surface P of the spheroid W, according to the distance and the thickness specified by the user, as shown in FIG. 19 (Step SB2).

Figure 20:
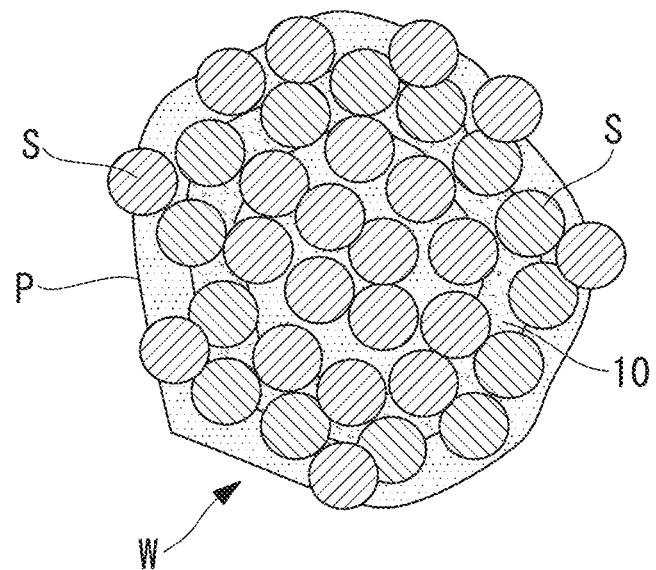
FIG. 20 is a view for explaining a state in which cells that overlap with the 3D mask shown in FIG. 19 are identified and displayed.
Figure 21:
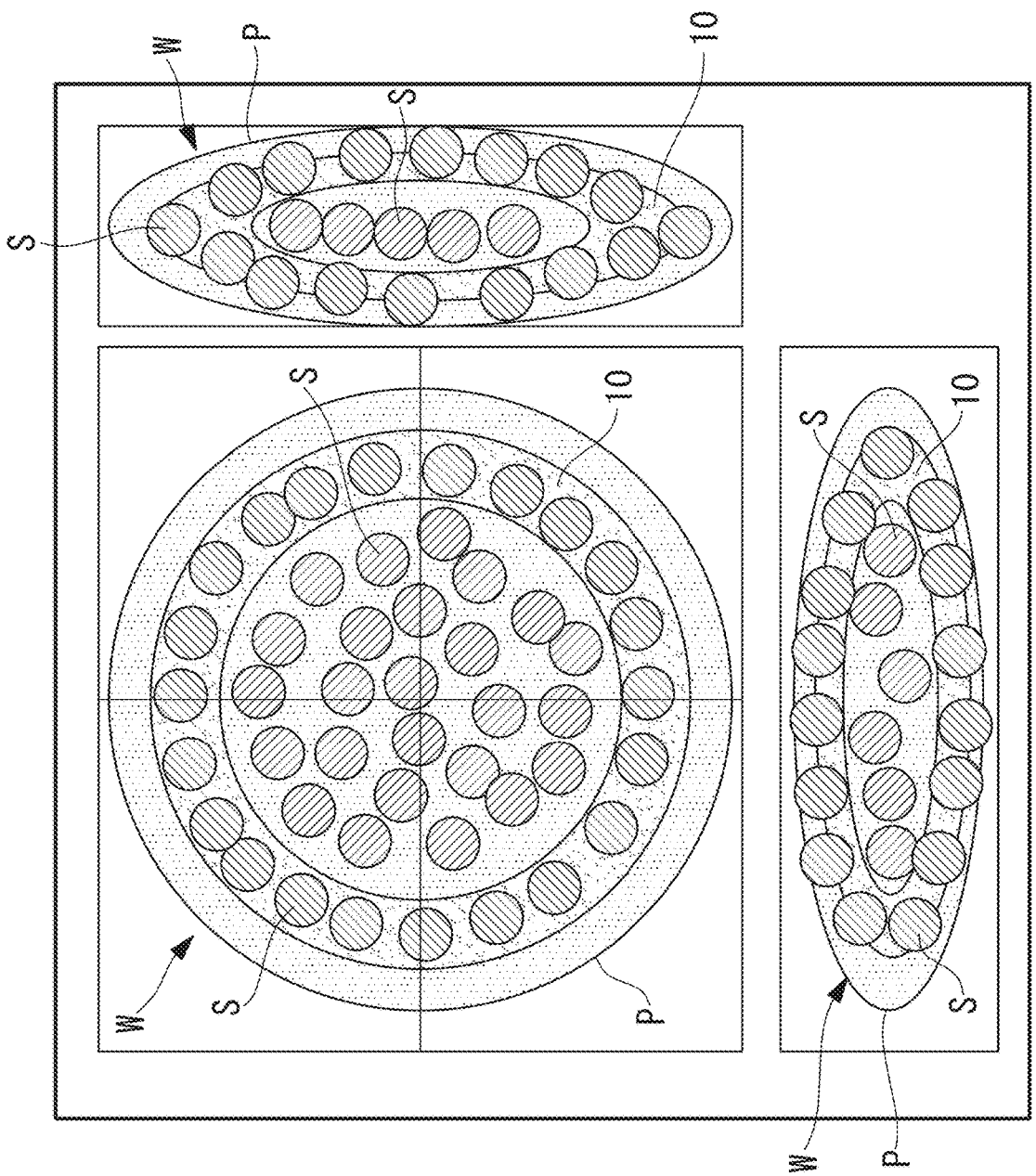
FIG. 21 is a view for explaining a state in which a 3D mask and cells are displayed on respective cross-sectional images in a distinguishable manner.

Steps SB3 to SB8 are the same as those in this embodiment. Accordingly, as shown in FIG. 20, cells S that overlap with the set 3D mask 10, i.e., cells S of which the centers of gravity of the nuclei are contained inside the 3D mask 10, are extracted by the CPU 71 (Step SB4). Then, as shown in FIG. 21, the CPU 71 displays, in the respective cross-sectional images, the region where the 3D mask 10 is set, regions where the 3D mask 10 is not set, the cells S that overlap with the 3D mask 10, and the cells S that do not overlap with the 3D mask 10, in different colors in a distinguishable manner (Step SB7).

By doing so, it is possible to set a 3D mask 10 that has a desired thickness at a desired position in the radial direction specified by the user and to selectively analyze cells S that exist in the 3D mask 10. For example, the thickness of the 3D mask 10 is set according to the size of a single cell S, and the position of the 3D mask 10 is shifted by gradually reducing the size of the 3D mask 10 while maintaining the thickness thereof, thereby making it possible to find the depth of the innermost layer in which the drug has an effect on the cells, from the circumscribed surface P of the spheroid W toward the inside thereof. In other words, it is possible to find the boundary between the layer of cells S on which the drug has an effect and the layer of cells S on which the drug has no effect.

Accordingly, for example, in a case in which an anticancer drug is administered from the outside of the spheroid W, it is possible to correctly evaluate the depth of the innermost layer in which cells S are killed. In a case in which a drug or a cosmetic is applied to skin, it is also possible to find the innermost layer in which cells S are adversely affected, i.e., to correctly evaluate toxicity with respect to the cells S, thereby making it possible to determine the safety.

Second Embodiment

Next, an observation system according to a second embodiment of the present invention will be described below.

Figure 22:
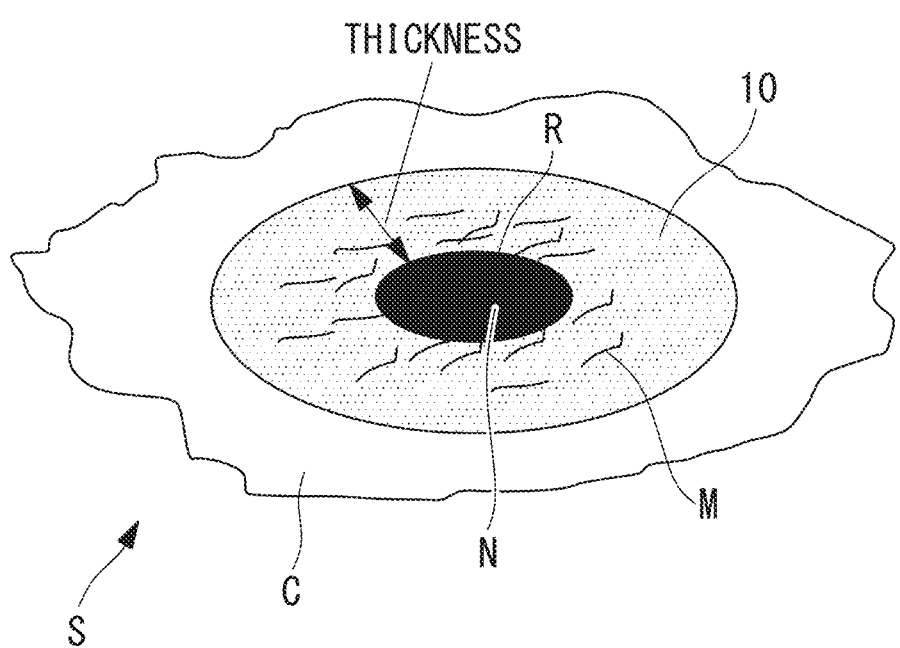
FIG. 22 is a view showing an example 3D mask that is set outside a circumscribed surface of a cell nucleus.

As shown in FIG. 22, the observation system 1 of this embodiment differs from that of the first embodiment in that an individual cell S serves as an observation target, and a 3D mask 10 is set outside a circumscribed surface R of the nucleus N of the cell S.

In the following explanation, identical reference signs are assigned to portions having configurations common to the observation system 1 of the first embodiment, and a description thereof will be omitted.

Through the execution of the recognition program, the CPU 71 applies recognition processing to individual cells S and organelles (cell components), such as mitochondria M, in a 3D image. The CPU 71 identifies the recognized individual cells S and organelles by assigning, thereto, labels different from one another and generates a label image and tables.

Through the execution of the 3D-mask generation program, the CPU 71 sets, inside the cell cytoplasm C, a 3D mask (similar region) 10 of which the radial distance from the circumscribed surface R of a 3D shape of the nucleus N of each of the recognized cells S is fixed over the entire region of the circumscribed surface R and of which the shape is similar to the circumscribed surface R. Specifically, according to the radial thickness of the 3D mask 10 specified by the user by means of the input unit 11, the CPU 71 sets, inside the cell cytoplasm C, a 3D mask 10 that extends outward from the circumscribed surface R by the corresponding thickness over the entire region of the circumscribed surface R of the nucleus N.

Through the execution of the measurement program, the CPU 71 identifies the organelles, such as mitochondria M, contained inside the set 3D mask 10 and extracts the corresponding organelles. For example, the CPU 71 may extract organelles of which the centers of gravity are contained inside the 3D mask 10. The CPU 71 creates data (information) of the extracted organelles. The data of the organelles can be the intensity of fluorescence, for example.

Through the execution of the display program, the CPU 71 displays the 3D mask 10 and the organelles, such as mitochondria M, contained inside the 3D mask 10, in an overlapping manner on the respective cross-sectional images displayed on the monitor 7 and also displays the organelles, such as mitochondria M, contained inside the 3D mask 10 and organelles, such as mitochondria M, contained outside the 3D mask 10, in different colors in a distinguishable manner. The CPU 71 displays graphs, such as a histogram and a scattergram, showing the created data of organelles such as mitochondria M, e.g., the brightness of fluorescence, on the monitor 7 side by side with the respective cross-sectional images.

With the input unit 11, the user can specify, as the thickness of the 3D mask 10, the thickness of a 3D mask 10, in the direction along the radial direction of the nucleus N of the cell S, that is to be set by the CPU 71 (hereinafter, referred to as the thickness of the 3D mask 10 in this embodiment). The thickness of the 3D mask 10 may be indicated in terms of the number of pixels or the distance, for example.

The operation of the thus-configured observation system 1 will now be described.

Because the way of acquiring a 3D image of a cell S by using the observation system 1 of this embodiment is the same as that in the first embodiment, a description thereof will be omitted, and a description will be given of a case in which a desired cell S is observed.

First, the CPU 71 executes the display program and displays the XY cross-sectional image, the XZ cross-sectional image, and the YZ cross-sectional image, which constitute a 3D image of the cell S, and the graphs, on the monitor 7 side by side in association with one another.

Then, as in the first embodiment, the CPU 71 executes the recognition program, recognizes the nuclei N and organelles, such as mitochondria M, of individual cells S in the 3D image, identifies them by assigning, thereto, labels different from one another, and generates a label image and tables.

Figure 23:
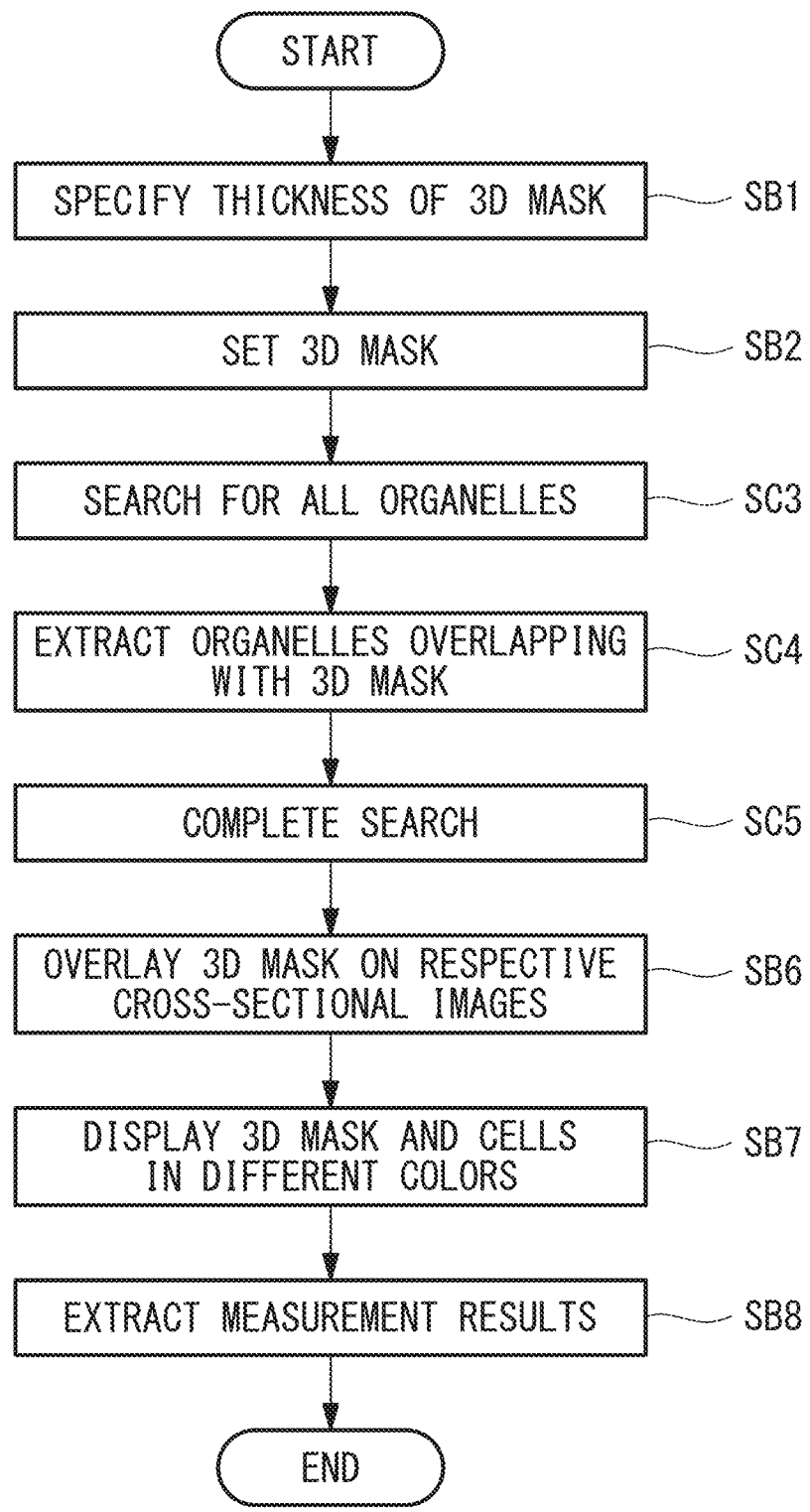
FIG. 23 is a flowchart for explaining 3D-mask generating processing performed by an observation system according to a second embodiment of the present invention.

Then, the CPU 71 executes the 3D-mask generation program. As shown in the flowchart of FIG. 23, when the user specifies the thickness of the 3D mask 10 so as to fit in the cell cytoplasm C, by means of the input unit 11 (Step SB1), the CPU 71 sets, inside the cell cytoplasm C, a 3D mask 10 that extends outward from the circumscribed surface R of the nucleus N of the cell S by the corresponding thickness over the entire region of the circumscribed surface R, according to the thickness specified by the user, as shown in FIG. 22 (Step SB2).

Then, the CPU 71 executes the measurement program, thus starting to search for all labelled organelles, such as mitochondria M, in the label image and the tables for the cells S and the organelles, which are stored in the disk 69 (Step SC3). Then, organelles, such as mitochondria M, that overlap with the set 3D mask 10 are extracted (Step SC4). When all organelles, such as mitochondria M, that overlap with the 3D mask 10 are extracted, the searching ends (Step SC5).

Then, the CPU 71 executes the display program, and the 3D mask 10 is overlaid on the XY cross-sectional image, the XZ cross-sectional image, and the YZ cross-sectional image, which are displayed on the monitor 7 (Step SB6). In the respective cross-sectional images, the region where the 3D mask 10 is set, regions where the 3D mask 10 is not set, the organelles, such as mitochondria M, that overlap with the 3D mask 10, the organelles, such as mitochondria M, that do not overlap with the 3D mask 10 are displayed in different colors in a distinguishable manner (Step SB7).

Furthermore, the CPU 71 executes the measurement program, and, as a result of measurement of the organelles, such as mitochondria M, that overlap with the 3D mask 10, the brightness of fluorescence, for example, is extracted and is displayed on the monitor 7 (Step SB8).

As described above, according to the observation system 1 of this embodiment, organelles, such as mitochondria M, that exist in a fixed region, inside an individual cell S, that does not contain the nucleus N can be selectively analyzed with accuracy. For example, it is possible to measure the state of organelles, such as mitochondria M, that exist within a fixed distance in the vicinity of the outer side of the nucleus N of the cell S.

In this embodiment, as in the modification of the first embodiment, it is also possible for the user to specify the thickness and the radial distance of the 3D mask 10 with reference to the nucleus N of the cell S and for the CPU 71 to set, inside the cell cytoplasm C, a 3D mask 10 that extends outward by the corresponding thickness at the position shifted from the circumscribed surface R by the corresponding distance, over the entire region of the circumscribed surface R of the nucleus N, according to the thickness and the radial distance specified by the user.

Furthermore, although descriptions have been separately given of the first embodiment and the second embodiment, for example, the user may select the spheroid W as an observation target, as in the first embodiment, or the nucleus N of an individual cell S as an observation target, as in the second embodiment, and the same processing as in the first embodiment and the second embodiment may be switched between and performed on the observation target selected by the user.

Although the embodiments of the present invention have been described above in detail with reference to the drawings, the specific configurations are not limited to those in the embodiments, and design changes etc. that do not depart from the scope of the present invention are also encompassed. For example, the present invention is not limited to the configurations applied to the above-described embodiments and can be applied to an embodiment obtained by appropriately combining the embodiments, without particular limitation.

As a result, the following aspects of the present invention are derived from the above-described embodiments.

According to one aspect, the present invention provides an observation system including at least one processor that is provided with hardware, wherein the at least one processor performs control so as to: recognize the 3D shape of an observation target from a 3D image of a fluorescent specimen; set a similar region of which the distance in a radial direction from a circumscribed surface of the recognized 3D shape is fixed over the entire region of the circumscribed surface and of which the shape is similar to the circumscribed surface; and identify a cell that is contained inside the set similar region or a cell component that constitutes the cell.

According to this aspect, the similar region, of which the shape is similar to the 3D shape of an observation target recognized from a 3D image of a fluorescent specimen, is set, and a cell or a cell component that is contained inside the similar region is identified. Because the radial distance of the set similar region from the circumscribed surface of the 3D shape of the observation target is fixed over the entire region of the circumscribed surface, it is possible to distinguish a cell or a cell component that exists within the fixed distance from a cell or a cell component that exists in the other locations. Therefore, a fixed region at an outer periphery or an inner periphery of an observation target of the fluorescent specimen, which has a three-dimensional structure, can be selectively analyzed with accuracy.

Here, when a drug is administered to an outer section of the fluorescent specimen, the drug infiltrates toward the inside of the fluorescent specimen, so that the effect of the drug with respect to a cell or a cell component that exists within the fixed distance from the circumscribed surface of the observation target can be correctly evaluated, separately from the effect of the drug with respect to a cell or a cell component that exists in the other locations.

The above-described aspect may further include a storage unit that stores at least one computer program to be executed by the at least one processor.

The above-described aspect may further include a thickness specifying unit that is configured to allow a user to specify a thickness in the radial direction of the similar region to be set, wherein the at least one processor may perform control so as to set the similar region according to the thickness specified by the user by means of the thickness specifying unit.

With this configuration, it is possible to selectively analyze a cell or a cell component that exists in a similar region that has a desired thickness specified by the user by means of the thickness specifying unit.

The above-described aspect may further include a distance specifying unit that is configured to allow a user to specify a distance in the radial direction from the circumscribed surface, which forms the similar region to be set, wherein the at least one processor may perform control so as to set the similar region according to the distance specified by the user by means of the distance specifying unit.

With this configuration, it is possible to selectively analyze a cell or a cell component that exists in a similar region that is located at a desired position in the radial direction specified by the user by means of the distance specifying unit.

The above-described aspect may further include a display unit that simultaneously displays three cross-sectional images that constitute the 3D image and that are perpendicular to one another, in association with one another, wherein the at least one processor may further perform control so as to display the similar region and the cell that is contained inside the similar region or the cell component, in an overlapping manner on the respective cross-sectional images displayed by the display unit and so as to display the cell that is contained inside the similar region or the cell component and the cell that is contained outside the similar region or the cell component, in a distinguishable manner.

With this configuration, the user can simultaneously visually recognize cross-sectional shapes of the observation target in three directions perpendicular to one another, from the three cross-sectional images of the 3D image, which are simultaneously displayed by the display unit. In this case, the similar region and a cell or a cell component that is contained inside the similar region are displayed on the respective cross-sectional images in an overlapping manner, thereby making it possible for the user to grasp the number of cells or cell components contained inside the similar region, at a glance. Furthermore, cells or cell components inside the similar region and outside the similar region are displayed on the respective cross-sectional images in a distinguishable manner, thereby making it possible for the user to easily and correctly distinguish a cell or a cell component that exists within the fixed distance from the circumscribed surface of the observation target from a cell or a cell component that exists in the other regions and to observe the cell or cell component.

In the above-described aspect, the at least one processor may further perform control so as to extract the cell that is contained inside the similar region or the cell component and to output information about the extracted cell or cell component.

With this configuration, the user can easily collect information about a cell or a cell component that exists within the fixed distance from the circumscribed surface of the observation target.

In the above-described aspect, the at least one processor may perform control so as to: recognize the 3D shape of a cell cluster formed by an aggregation of a plurality of cells cluster serving as the observation target; set the similar region inside the circumscribed surface of the cell cluster; and identify the cell that is contained inside the similar region.

With this configuration, a cell that exists in a fixed region inside the cell cluster can be selectively analyzed with accuracy.

In the above-described aspect, the at least one processor may perform control so as to: recognize the 3D shape of a nucleus of the cell that serving as the observation target; set the similar region outside the circumscribed surface of the nucleus of the cell; and identify the cell component that is contained inside the similar region.

With this configuration, a cell component that exists in a fixed region inside an individual cell can be selectively analyzed with accuracy.

According to another aspect, the present invention provides a non-transitory computer-readable medium that stores a computer-readable program for implementing a control method for controlling an observation system, the method including: a step of recognizing the 3D shape of an observation target from a 3D image of a fluorescent specimen; a step of setting a similar region of which the distance in a radial direction from a circumscribed surface of the recognized 3D shape is fixed over the entire region of the circumscribed surface and of which the shape is similar to the circumscribed surface; and a step of identifying a cell that is contained inside the set similar region or a cell component that constitutes the cell.

REFERENCE SIGNS LIST 1 observation system
7 monitor (display unit)
10 3D mask (similar region)
11 input unit (thickness specifying unit, distance specifying unit)
71 CPU (shape recognition unit, similar-region setting unit, identifying unit, display control unit, extraction unit)
P, R circumscribed surface
S cell (fluorescent specimen)

The invention claimed is:

1. An observation system comprising at least one processor that is provided with hardware,
wherein the at least one processor is configured to perform control so as to:
recognize a 3D shape of an observation target from a 3D image of a cell cluster formed by an aggregation of a plurality of cells serving as the observation target;
set a similar region a distance of which in a radial direction from a circumscribed surface of the recognized 3D shape is fixed over an entire region of the circumscribed surface and a shape of which is similar to the circumscribed surface, the similar region being set according to a thickness, that is specified by a user, in the radial direction of the similar region;
identify a cell that is contained inside the set similar region or a cell component that constitutes the cell; and display, on a display, at least one cross-sectional image of the 3D image on which the similar region and the cell or cell component that is contained inside the similar region is displayed in an overlapping manner.

2. The observation system according to claim 1, further comprising a storage that stores at least one computer program to be executed by the at least one processor.

3. The observation system according to claim 1, further comprising an input device that is configured to accept input from the user,
wherein the at least one processor is further configured to perform control so as to set the similar region according to a distance, that is specified by the user, in the radial direction from the circumscribed surface, and
wherein each of the thickness and the distance is specified by the user using the input device.

4. The observation system according to claim 3, wherein the at least one processor is further configured to perform control so as to extract the cell or the cell component that is contained inside the similar region and to output information about the extracted cell or cell component.

5. The observation system according to claim 1, further comprising the display,
wherein the at least one processor is further configured to perform control so as to display, on the display, three cross-sectional images that constitute the 3D image and that are perpendicular to one another, in association with one another, and
wherein the at least one processor is further configured to perform control so as to display the similar region and the cell or the cell component that is contained inside the similar region in an overlapping manner on the respective cross-sectional images displayed on the display in such a way that the cell or the cell component that is contained inside the similar region is displayed in a manner distinguishable from the cell or the cell component that is contained outside the similar region.

6. The observation system according to claim 1, wherein the at least one processor is further configured to perform control so as to:
recognize the 3D shape of the cell cluster;
set the similar region inside the circumscribed surface of the cell cluster; and
identify the cell that is contained inside the set similar region.

7. The observation system according to claim 1, wherein the at least one processor is further configured to perform control so as to:
recognize the 3D shape of a nucleus of the cell;
set the similar region outside the circumscribed surface of the nucleus of the cell; and
identify the cell component that is contained inside the set similar region.

8. A non-transitory computer-readable medium that stores a computer-readable program for implementing a control method for controlling an observation system, the method comprising:
recognizing a 3D shape of an observation target from a 3D image of a cell cluster formed by an aggregation of a plurality of cells serving as the observation target;
setting a similar region distance of which in a radial direction from a circumscribed surface of the recognized 3D shape is fixed over an entire region of the circumscribed surface and a shape of which is similar to the circumscribed surface, the similar region being set according to a thickness, that is specified by a user, in the radial direction of the similar region;
identifying a cell that is contained inside the set similar region or a cell component that constitutes the cell; and
displaying, on a display, at least one cross-sectional image of the 3D image on which the similar region and the cell or cell component that is contained inside the similar region is displayed in an overlapping manner.

* * * * *